United States Patent
Swain et al.

(10) Patent No.: US 7,494,496 B2
(45) Date of Patent: Feb. 24, 2009

(54) DEVICE FOR TRANSFIXING AND JOINING TISSUE

(75) Inventors: Christopher Paul Swain, London (GB); Charles Alexander Mosse, London (GB)

(73) Assignee: UCL BioMedica PLc, London (GB)

( * ) Notice: Subject to any disclaimer, the term of this patent is extended or adjusted under 35 U.S.C. 154(b) by 301 days.

(21) Appl. No.: 10/990,833

(22) Filed: Nov. 16, 2004

(65) Prior Publication Data

US 2005/0113851 A1 May 26, 2005

Related U.S. Application Data

(63) Continuation of application No. PCT/GB03/02075, filed on May 14, 2003.

(30) Foreign Application Priority Data

May 17, 2002 (GB) .................................. 0211378.5

(51) Int. Cl.
*A61B 17/08* (2006.01)
(52) U.S. Cl. ..................................... 606/151
(58) Field of Classification Search ................ 606/232, 606/72, 151, 157, 213, 215, 122, 158; 24/132 R, 24/298; 63/38; 446/487
See application file for complete search history.

(56) References Cited

U.S. PATENT DOCUMENTS

| 3,209,422 A | * | 10/1965 | Dritz .......................... 24/706 |
| 3,820,535 A | * | 6/1974 | Marco ......................... 128/839 |
| 3,845,772 A | * | 11/1974 | Smith .......................... 606/232 |
| 5,041,129 A |   | 8/1991 | Hayhurst et al. |
| RE34,021 E | * | 8/1992 | Mueller et al. ............... 604/533 |
| 5,269,809 A | * | 12/1993 | Hayhurst et al. ............. 606/232 |
| 5,417,691 A | * | 5/1995 | Hayhurst ...................... 606/72 |
| 5,613,939 A | * | 3/1997 | Failla .......................... 600/201 |
| 5,645,589 A |   | 7/1997 | Li |
| 5,725,556 A | * | 3/1998 | Moser et al. ................. 606/232 |
| 5,810,851 A | * | 9/1998 | Yoon ........................... 606/148 |
| 5,845,645 A | * | 12/1998 | Bonutti ....................... 128/898 |
| 6,071,292 A |   | 6/2000 | Makower et al. |
| 6,117,160 A | * | 9/2000 | Bonutti ....................... 606/215 |
| 6,287,325 B1 |   | 9/2001 | Bonutti |

OTHER PUBLICATIONS

"Anastomosis at flexible endoscopy; an experimental study of compression button gastrojejunostomy", C. Swain, et al., Gastrointestinal Endoscopy, pp. 628-631, Nov. 1991.

* cited by examiner

*Primary Examiner*—Todd E Manahan
*Assistant Examiner*—Ryan Severson
(74) *Attorney, Agent, or Firm*—Blakely, Sokoloff, Taylor & Zafman LLP

(57) ABSTRACT

A device is provided which can act as one component of an anastomosis-forming assembly, i.e. as an anastomosis button. The device comprises a plurality of elongate members having a first, introduction configuration in which they are substantially aligned with one another, and a second, use configuration in which they are disposed at an angle to one another. For example, there may be two such elongate members, which, in the use configuration, form a cross. The device comprises means, for example, a tensionable thread, for bringing the elongate members into the use configuration.

5 Claims, 4 Drawing Sheets

DEVICE FOR TRANSFIXING AND JOINING TISSUE

The present patent application is a continuation of International Application No. PCT/GB03/02075, filed May 14, 2003.

BACKGROUND

1. Field

This invention relates to methods and devices for transfixing and joining tissues and, more particularly, to forming anastomoses.

2. Description of the Related Art

In abdominal and vascular surgery anastomosis, the joining together of hollow structures, is an important goal. The ability to establish continuity between two hollow structures can relieve blockage due to cancer, inflammation or other pathology, can allow the removal of abnormal tissue or organs, and by bypassing a blocked segment, can allow the unimpeded movement of food or facilitate the flow of blood or bile through the body.

Anastomoses are most commonly formed at open abdominal surgery (laparotomy). Hand sewn anastomoses, usually in two or even three layers, are widely performed but are time consuming and require large incisions for hand access. Stapled anastomoses became widely performed especially in colonic surgery since they allowed surgeons to remove low rectal tumours. The short rectal remnant could be joined to the colon above the tumour at a site where it was difficult to place stitches by hand, and in consequence allowed patients to recover without needing a permanent colostomy. The advent of laparoscopic surgery staplers allowed anastomoses to be formed through incisions of 1-2 cm or so that were just large enough to allow passage of these instruments inside the abdominal or thoracic cavity.

Some aids so form anastomoses have been developed. J. B. Murphy, an American surgeon working in Chicago in the 1880's, popularized surgical astomoses by creating a compression button device for anastomosis. The device had two mushroom-shaped buttons, which could be placed in the two organs to be joined. The buttons could be pressed together by an internal spring in the stalk of the mushroom and the organs would be welded together by the consequent ischaemia (lack of blood supply) at the sites where the buttons were pressed together. Eventually the button device would fall through into the gut, leaving an anastomosis or hole and be passed through the body into the toilet. Compression button anastomoses are still used at open colonic surgery. The use of magnets to compress tissue to form an anastomosis has also been described, and a spring compression button method using a biofragmentable ring has been employed, especially in the rectum.

An anastomosis procedure has been described in an article entitled "Anastomosis at Flexible Endoscopy: an experimental study of compression button gastrojejunoscopy", C P Swain and T N Mills, Gastrointestinal Endoscopy 1991, 37: 625-631, in which, as its title implies, a method is described of forming anastomoses using a flexible endoscope. The method described there involved introducing a flexible endoscope into one of the two structures to be joined (in this case the stomach), and entering the second of the two structures (in this case the small bowel) by forming an incision in the abdomen of the subject. The present invention is directed, in one aspect thereof, to the formation of anastomoses without the need to make such external incisions, though the invention is also applicable to the formation of anastomoses by procedures in which such incisions are made.

The ability to form anastomoses using flexible endoscopic or percutaneous procedures without opening the abdomen or chest or using laparoscopic methods might offer advantages especially to patients with advanced cancer or in elderly or sick patients, who might withstand conventional surgery poorly. In particular, flexible endoscopy might allow anastomoses to be formed from stomach to small bowel, duodenum to gallbladder, and small bowel to colon.

Flexible endoscopy allows access to many hollow organs including oesophagus, stomach, duodenum, small intestine and colon, and most flexible endoscopes have a channel through which instruments can be passed. Although the flexible endoscopes employed for most conventional purposes do not provide information on the location of tubular structures outside the organ, modified flexible endoscopes employing ultrasound are available which do. Endoscopic ultrasound is a hybrid method, which uses ultrasound imaging at the tip of the endoscope but returns the optical imaging and internal instrument channel of a conventional endoscope. Some such endoscopes have their imaging array constructed in a linear fashion, which allows good ultrasound visualization of organs adjacent to the organ in which the tip of the endoscope lies.

Devices are described here which can form anastomoses either through flexible endoscopes or at percutaneous needle access, which do not require surgical incision or laparoscopy (although they might be used during either of these surgical methods to form an anastomosis), and which may be used in combination with ultrasound or x-ray imaging externally to the patient or, preferably, imaging internally to the patient, for example using endoscopic ultrasound. In this situation the particular problem may arise that there may be no access to the distal side of the tissues to be joined except by making a hole through the tissues themselves, so the anastomosis-forming component on the distal side of the tissue layers must be thin enough to fit through a hole without causing excessive trauma to the tissues.

SUMMARY

According to the present invention there is provided a device adapted to act as a first component, in cooperation with a second component, for use in bringing together a first tissue layer and a second tissue layer, preferably to form a anastomosis. The device comprises a plurality of elongate members having a first configuration in which they are substantially aligned with one another, and a second configuration in which they are disposed at an angle to one another, the device comprising means for bringing the elongate members from the first configuration to the second configuration. When the elongate members are in the first configuration they are able to pass down a tube to the site of use, and then successively, through small aligned holes formed in the first and second tissue layers. When they are then brought into their second configuration their collective cross-section is such that they cannot return through those holes, and a pulling force exerted on the elongate members will tend to urge the second tissue layer towards the first.

BRIEF DESCRIPTION OF THE SEVERAL VIEWS OF THE DRAWINGS

Two embodiments of the invention are shown in the accompanying diagrammatic drawings, in which.

DETAILED DESCRIPTION

Figure 1:
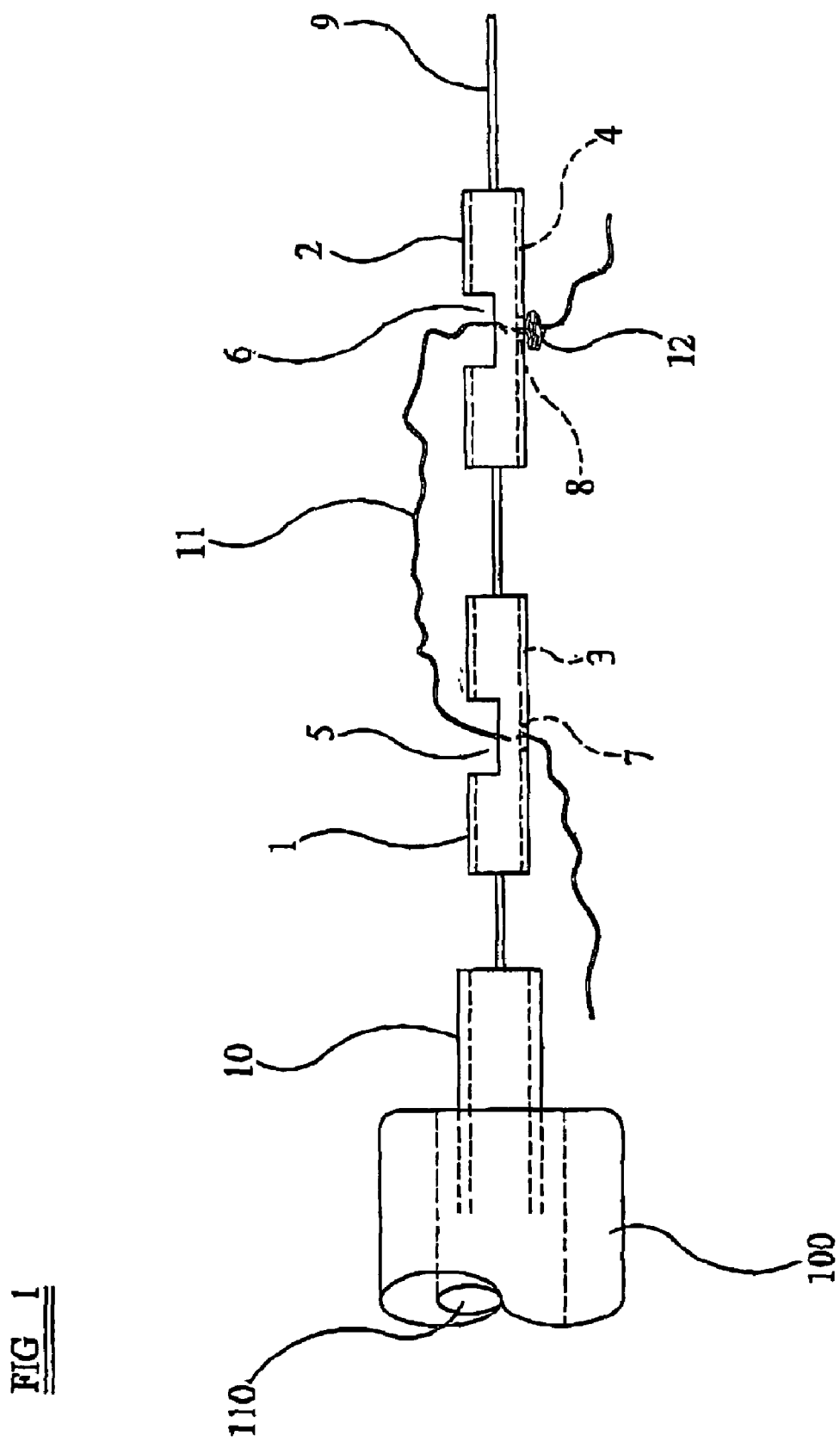
FIG. 1 shows the first embodiment with its elongate members in their first configuration.

The first embodiment comprises two hollow tubes 1 and 2, each having a respective bore 3, 4. The bores communicate with the exterior not only at their longitudinal ends but also each communicate via a respective notch 5, 6 and a respective aperture 7, 8, provided in their walls. The elongate members 1, 2 are threaded on a guide wire 9 which extends through their bores 3,4 and along a tube 10, e.g. a catheter tube made of a tight wound wire sheathed in a plastics material. In this particular embodiment, the assembly is shown emerging from the biopsy channel 110 of an endoscope 100.

The elongate members 1, 2 are brought to the intended site of use within a patient by placing the distal end of the tube adjacent that site, extending the guide wire 9 therefrom, pushing the wire through the tissues to be joined, then threading the elongate members onto the proximal end of the guide wire and running them down the interior of the biopsy channel 110 with the aid of the tube 10. For this purpose, the internal diameter of the tube 10 must, of course, be less than the external diameter of the elongate members 1, 2. If it is assumed for present purposes that the device of FIG. 1 is to be used as one component of an anastomosis-forming device, the anastomosis being formed between first and second tissue layers, of which the first layer is that nearer to the point of entry (e.g. the mouth) of the tube into the patient, the distal end of the guide wire 9 will need to be positioned on the side of the second tissue layer which is remote from the first, and the elongate members will need to be pushed by the tube 10 through both tissue layers, so that they lie on that side of the second tissue layer.

As shown in FIG. 1, the elongate members are connected by a thread 11 which, as considered from its proximal to its distal ends, extends from outside the patient, along the gap between 10 and 110, then into the bore 3 of the elongate member 1 via the aperture 7 and out of that bore via the notch 5, into the bore 4 of the elongate member 2 via the notch 6, and out of the bore 4 via the aperture 8, at which point a knot 12 is formed which is of a greater size than can pass through the aperture 8.

Figure 2:
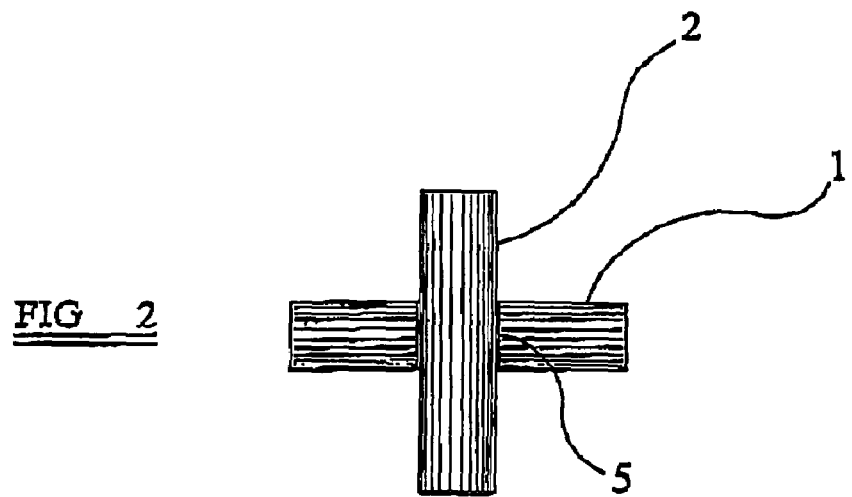
FIG. 2 shows the first embodiment with the elongate members in their second configuration.

With the elongate members 1, 2 in position, the guide wire 9 is pulled back out of the elongate members 1, 2, then tension is placed on the thread 11, which causes the elongate members 1, 2 to assume the second configuration shown in FIG. 2. This configuration is in the form of a cross, with those portions of the members which have the notches 5 and 6 formed therein, engaging one another. It will be appreciated that continued tension imparted to the thread 11 causes the elongate members 1, 2 to bear against the remote side of the second tissue layer, drawing it towards the first. If suitable moans is provided on the proximal side of the first tissue layer to prevent its moving in response to the force applied to the distal side of the second tissue layer, the two tissue layers will be compressed, thereby providing the conditions for an anastomosis to be formed.

Figure 5:
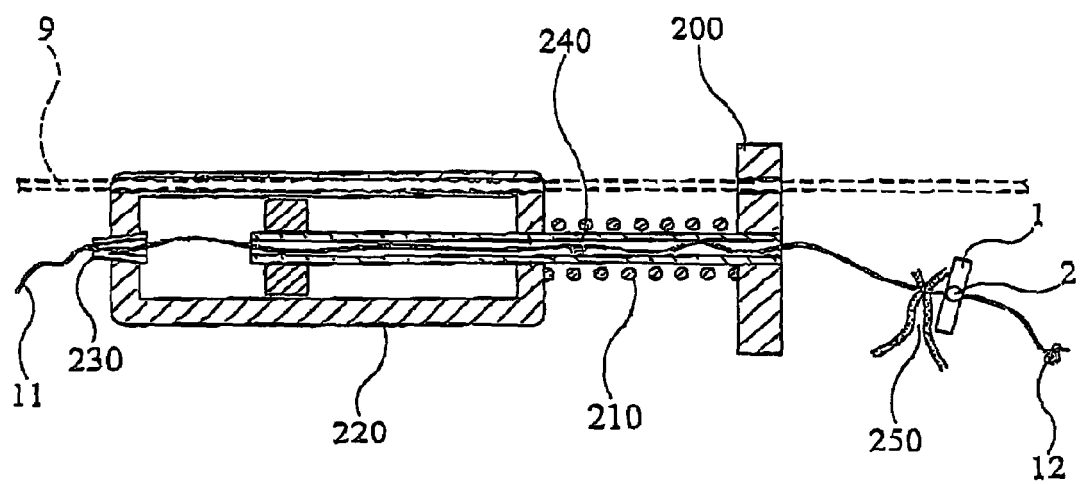
FIG. 5 shows an assembly which may be used to provide the second component of the anastomosis-forming device.

The anastomosis-forming component on the proximal side of the first tissue layer may be of any desired form and could, for example, be similar to one of the sprung mushrooms used in a Murphy button. FIG. 5 illustrates one way of providing the proximal button. It shows an assembly that has been used in experiments where it has been placed in the stomach, and which may also be used in contents other than in conjunction with the distal component described herein. It thus represents a further inventive concept. After the endoscope has been removed, the thread 11 is threaded through the assembly which is pushed into the stomach over the guide wire 9 with the aid of a tube, such as tube 10, passed over the thread 11 and pushing against the body of the device 220. Once the button 200 is pressing onto the proximal side of the tissues 250 to be anatomosed, the spring 210 is compressed by pulling back on the thread 11 whilst pushing forward on the body of the device 220 with the aid of the tube 10. The tapered hole 230 and the knot 240 act as a ratchet so that the spring remains compressed once the pushing tube 10 has been released and the excess tread proximal to the assembly has been cut.

Various modifications are possible to the arrangement shown in FIG. 5 for the proximal side of the first tissue layer. For example, the device 220 can be reduced in diameter so that all or part of it can be within a channel of the endoscope, and a pushing force may be exerted on the button by the endoscope, rather than by the tube 10 as described above.

Figure 4:
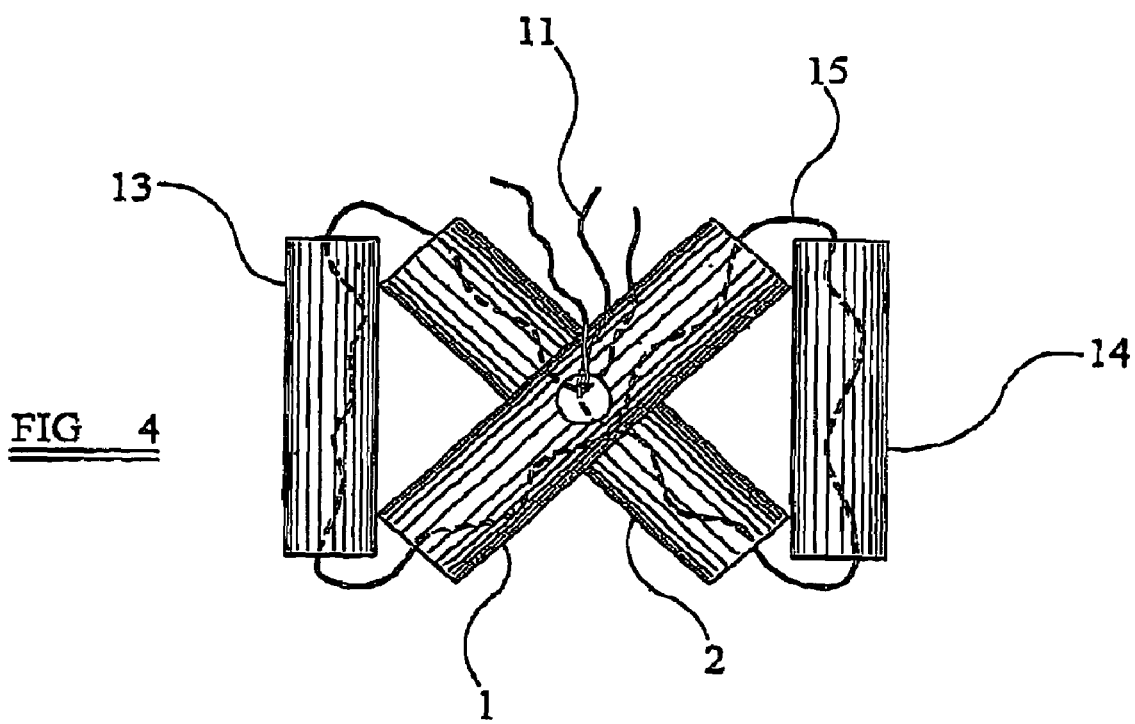
FIG. 4 shows the second embodiment with the elongate members in their second configuration.
Figure 3:
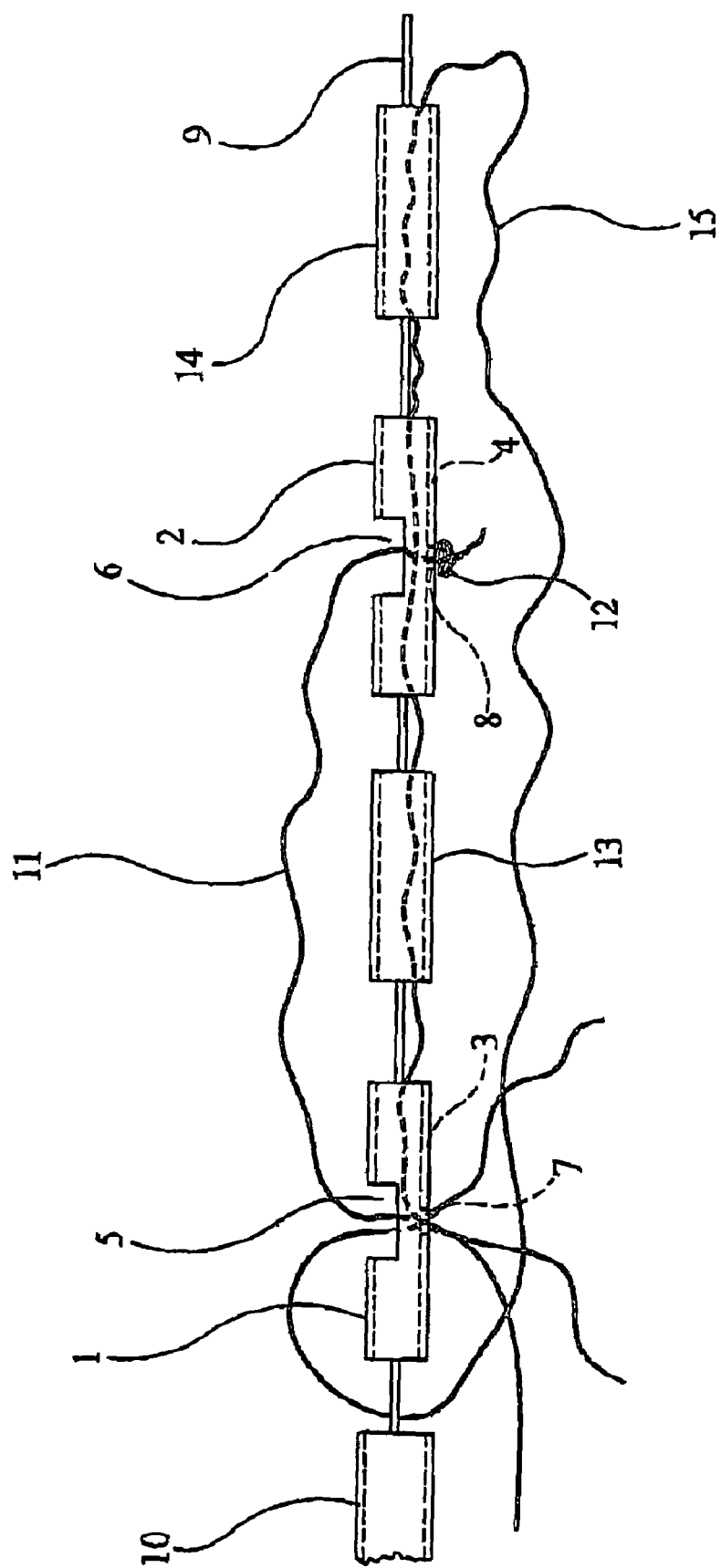
FIG. 3 shows the second embodiment with the elongate members in their first configuration.

FIGS. 3 and 4 show a second embodiment of the invention. This comprises four elongate members. Components in this embodiment which are common to the first embodiment are given the same reference numerals as in FIGS. 1 and 2, and will not be described further in detail at this point. The additional elements in the second embodiment consist of two tubes 13, 14 and a second thread 15. The tube 13 is threaded on the guide wire 9 intermediate the elongate members 1 and 2, and the tube 14 is threaded on the guide wise on the distal side of the elongate member 2. The thread 15, as considered from one of its ends, passes parallel to the tube 10 and therefore, up to the distal end of that tube, parallel to the thread 11, into the bore 3 of the elongate member 1 and out through the distal end of the that bore, thence successively through the bores of the tube 13, elongate member 2 and tube 14, from there into the bore 3 of the elongate member 1 via the notch 5 and out through the aperture 7. This end of the thread then passes back out of the patient, running parallel to the first portion of the thread.

The elements of the second embodiment are positioned at the intended site of use in the same way as for the first embodiment, and tension is then imparted to both threads. This brings the device into the second configuration shown in FIG. 4.

It will be understood that although the two illustrated embodiments comprise respectively two and four elements, it is within the scope of the present invention for there to be some other number of elements, provided always that a plurality is present.

The invention claimed is:

1. A device adapted to act as a first component, in cooperation with a second component, for use in bringing together a first tissue layer and a second tissue layer, the device comprising a plurality of separate elongate members each of which has a longitudinal axis, the device having a first, introduction configuration in which the longitudinal axes of the elongate members are substantially aligned with one another, and a second, use configuration in which the said longitudinal axes are disposed at an angle to one another, the device comprising means for bringing the elongate members from the first configuration to the second configuration, wherein the elongate members are tubular members having a tubular wall, the means for bringing the elongate members from the first configuration to the second configuration comprises a thread on which the elongate members are threaded, the elongate members being arranged to be brought into the second configuration by imparting tension to the thread, the elongate members each provided with a pair of openings in its respective tubular wall, the said thread passing successively through the pair of openings formed in the wall of one member and the pair of openings formed in the wall of the other member, and the device further comprising two additional tubes, and a second thread which passes successively through the first said tubular member, a first one of the said additional tubes, the said second tubular member, and a second one of the said additional tubes, whereby imparting tension to both threads brings the device into its second configuration, in which the said elongate members form a diagonal cross, and the said additional tubes lie in either side of the cross.

2. The device according to claim 1, wherein there are exactly two said elongate members which, in the said second configuration, form a cross.

3. The device according to claim 1, wherein each pair of said openings, comprises one which is in the form of a notch, the thread passing out of one of the elongate members through the notch formed therein and into the other of the elongate members through the notch formed therein, whereby the portions of the elongate members which have the notches formed therein engage one another when the elongate members are in the said second configuration.

4. A device adapted to act as a first component, in cooperation with a second component, for use in bringing together a first tissue layer and a second tissue layer, the device comprising:

a plurality of elongate members each of which has a longitudinal axis, the device having a first, introduction configuration in which the longitudinal axes of the elongate members are substantially aligned with one another, and a second, use configuration in which the said longitudinal axes are disposed at an angle to one another, means for bringing the elongate members from the first configuration to the second configuration, wherein the elongate members are tubular members having a tubular wall, and the means for bringing the elongate members from the first configuration to the second configuration comprises a thread on which the elongate members are threaded, the elongate members being arranged to be brought into the second configuration by imparting tension to the thread, two said elongate members are each provided with a pair of openings in its respective tubular wall, the said thread passing successively through the pair of openings formed in the wall of one member and the pair of openings formed in the wall of the other member, and two additional tubes, and a second thread which passes successively through the first said tubular member, a first one of the said additional tubes, the said second tubular member, and a second one of the said additional tubes, whereby imparting tension to both threads brings the device into its second configuration, in which the said elongate members form a diagonal cross, and the said additional tubes lie in either side of the cross.

5. The device according to claim 4, wherein each pair of said openings, comprises one which is in the form of a notch, the thread passing out of one of the elongate members through the notch formed therein and into the other of the elongate members through the notch formed therein, whereby the portions of the elongate members which have the notches formed therein engage one another when the elongate members are in the said second configuration.

\* \* \* \* \*